United States Patent [19]
Johnson

[11] Patent Number: 5,328,367
[45] Date of Patent: Jul. 12, 1994

[54] METHOD AND APPARATUS FOR APPLYING GUTTA PERCHA TO A CARRIER

[76] Inventor: William B. Johnson, 5010 E. 68th St., Ste. 104, Tulsa, Okla. 74136

[21] Appl. No.: 48,432

[22] Filed: Apr. 14, 1993

[51] Int. Cl.5 ............................................. A61G 5/02
[52] U.S. Cl. ..................................... 433/81; 433/224
[58] Field of Search ........................... 433/81, 90, 224

[56] References Cited

U.S. PATENT DOCUMENTS

| | | | |
|---|---|---|---|
| 3,581,399 | 6/1971 | Dragan | 433/90 |
| 4,684,344 | 8/1987 | Brockway et al. | 433/81 |
| 4,746,292 | 5/1988 | Johnson | 433/141 |
| 4,758,156 | 7/1988 | Johnson | 433/81 |
| 4,892,481 | 1/1990 | Kopunek et al. | 433/90 |
| 4,894,011 | 1/1990 | Johnson | 433/81 |
| 5,067,900 | 11/1991 | McSpadden | 433/81 |
| 5,085,586 | 2/1992 | Johnson | 433/224 |
| 5,089,183 | 2/1992 | Johnson | 264/16 |
| 5,098,298 | 3/1992 | Johnson | 433/224 |
| 5,118,297 | 6/1992 | Johnson | 433/224 |
| 5,149,268 | 9/1992 | Johnson | 433/224 |
| 5,161,973 | 11/1992 | Johnson | 433/221 |
| 5,190,702 | 3/1993 | Johnson | 264/16 |
| 5,215,461 | 6/1993 | Riazi | 433/81 |

Primary Examiner—John J. Wilson
Attorney, Agent, or Firm—Head & Johnson

[57] ABSTRACT

The present invention is an improved method and device used in applying gutta percha to a carrier which will later be used in filling and sealing an interior of a tooth after a root canal has been performed on the tooth. The method consists of inserting a gutta percha filled cannula into the barrel cavity of a syringe-type device, heating the cannula in order to increase the plasticity of the gutta percha, inserting a carrier into the cannula at the dispensing end of the syringe-type device and pushing a plunger of the syringe-type device downward in order to push the carrier, which is now coated with the gutta percha previously contained in the cannula, out of the dispensing end of the cannula. The gutta percha coated carrier is then ready for use in the root canal.

An alternate embodiment of the syringe-type device employs a modified plunger to accommodate an alternate cannula which is provided with its own dispensing cannula plunger.

23 Claims, 5 Drawing Sheets

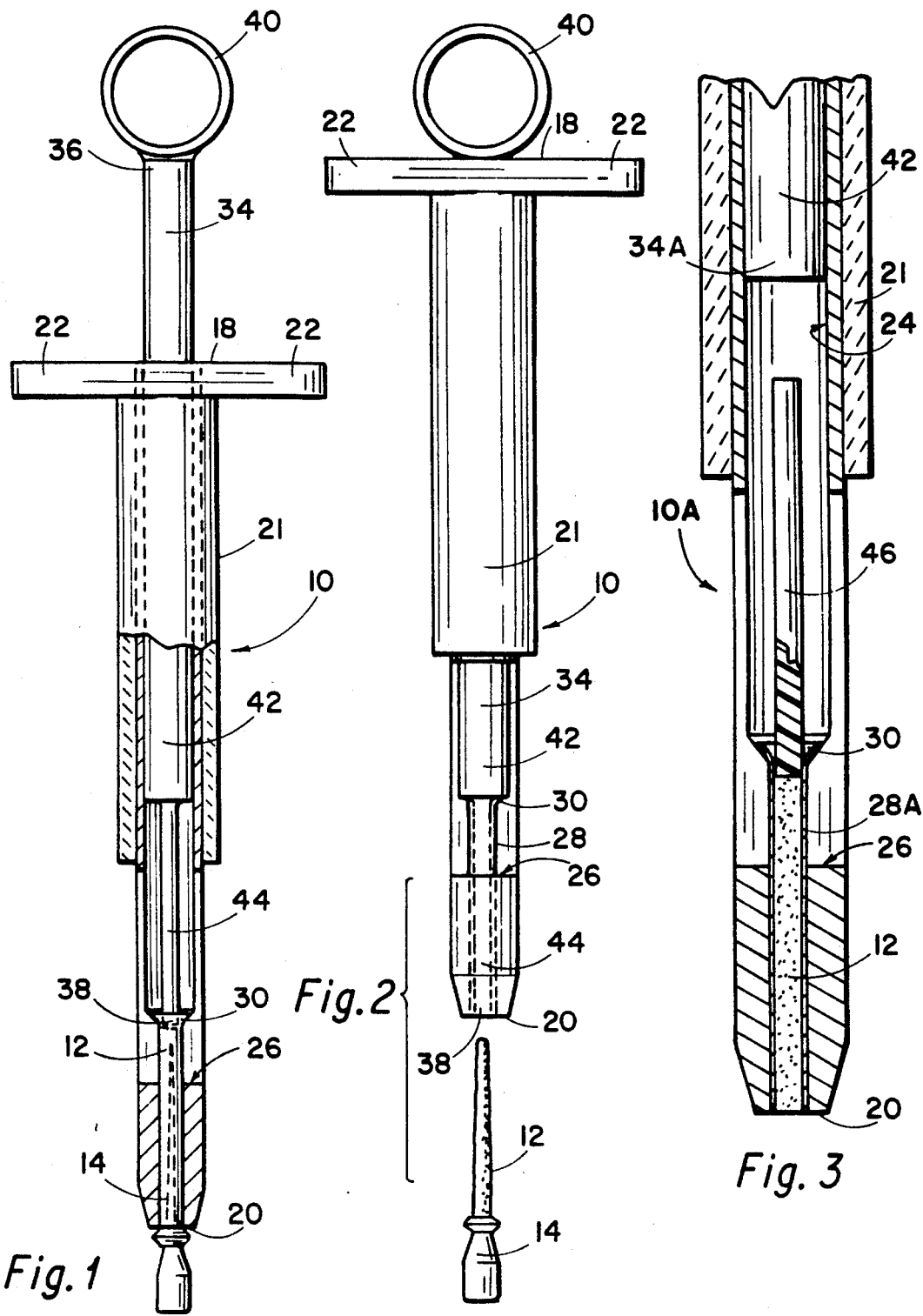

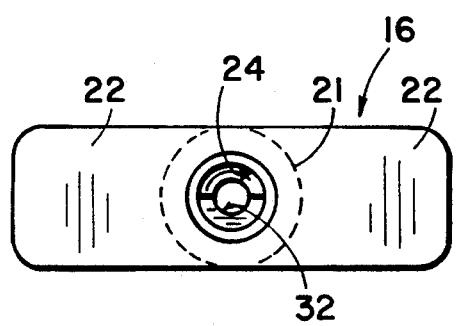

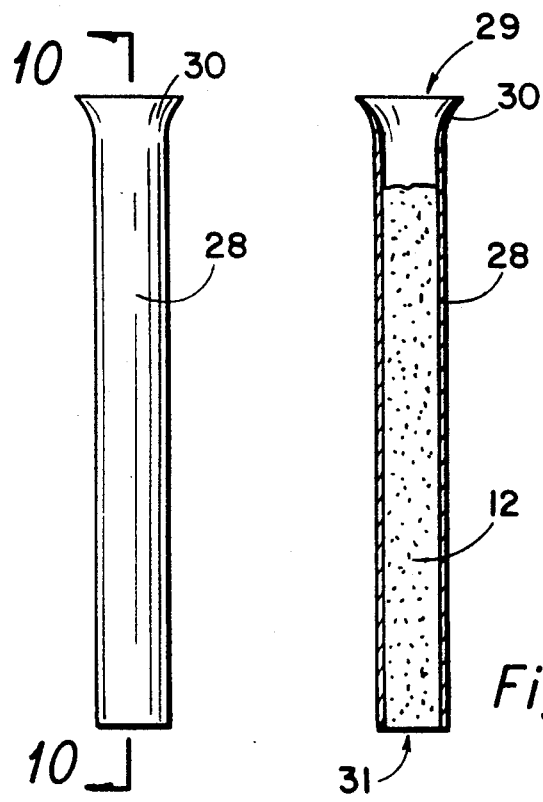
Fig. 9
Fig. 10
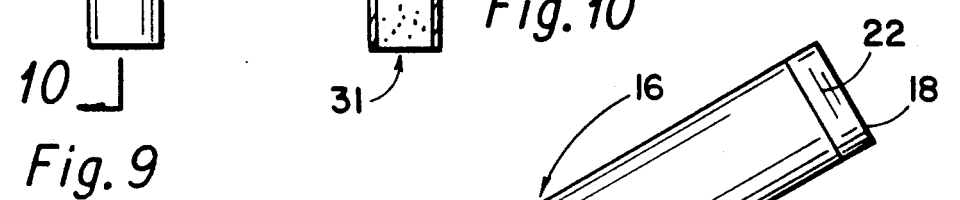
Fig. 11
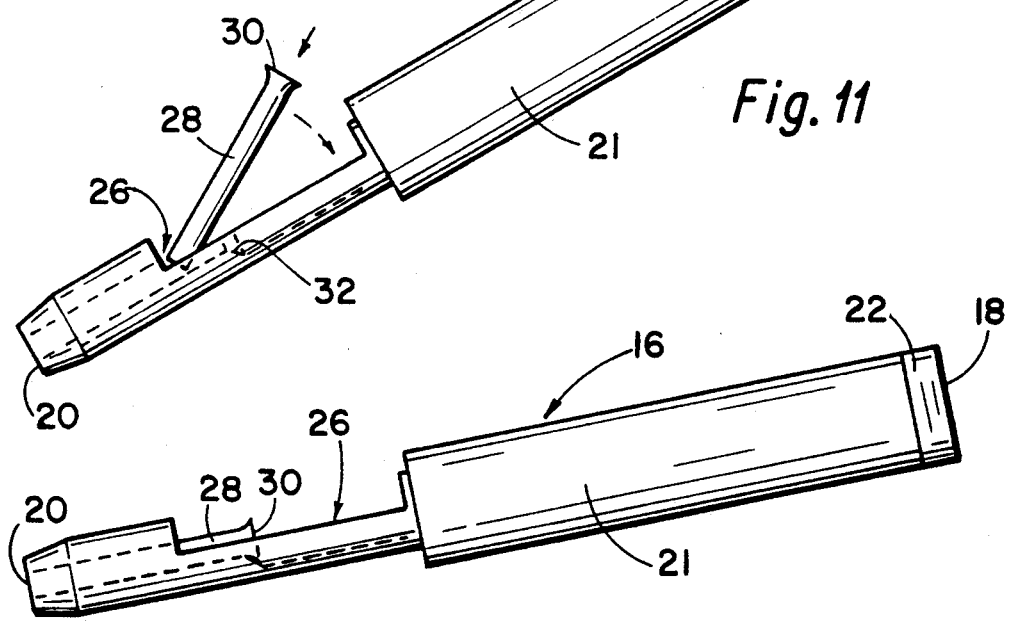
Fig. 12
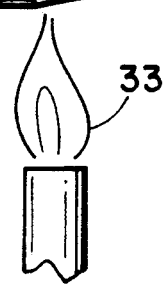

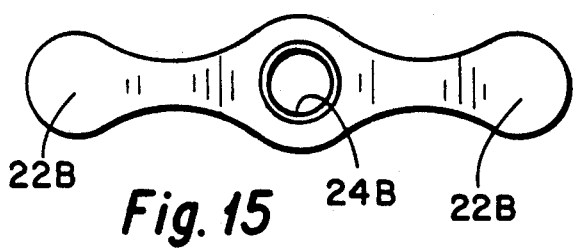
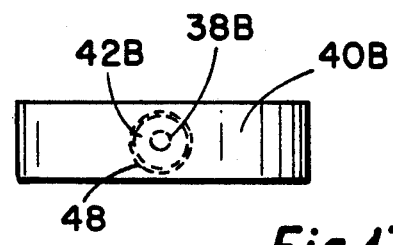
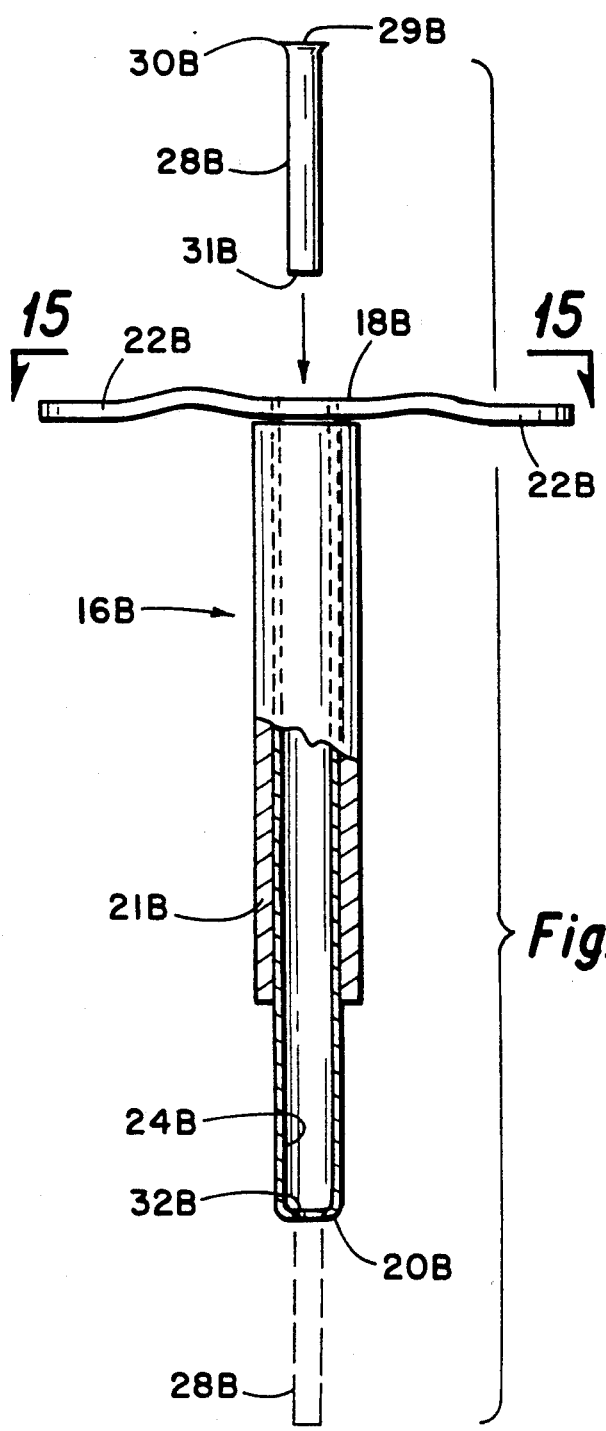
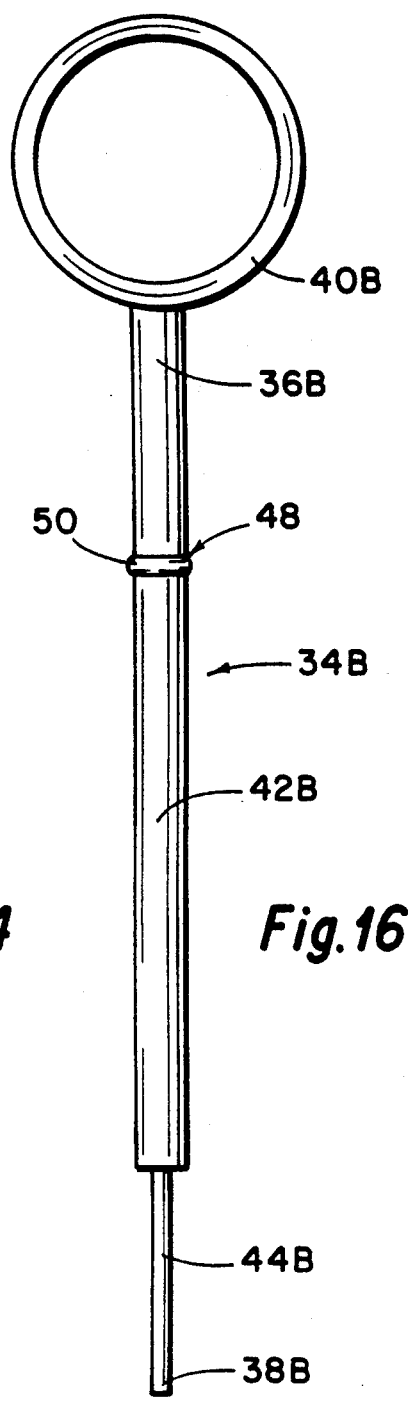

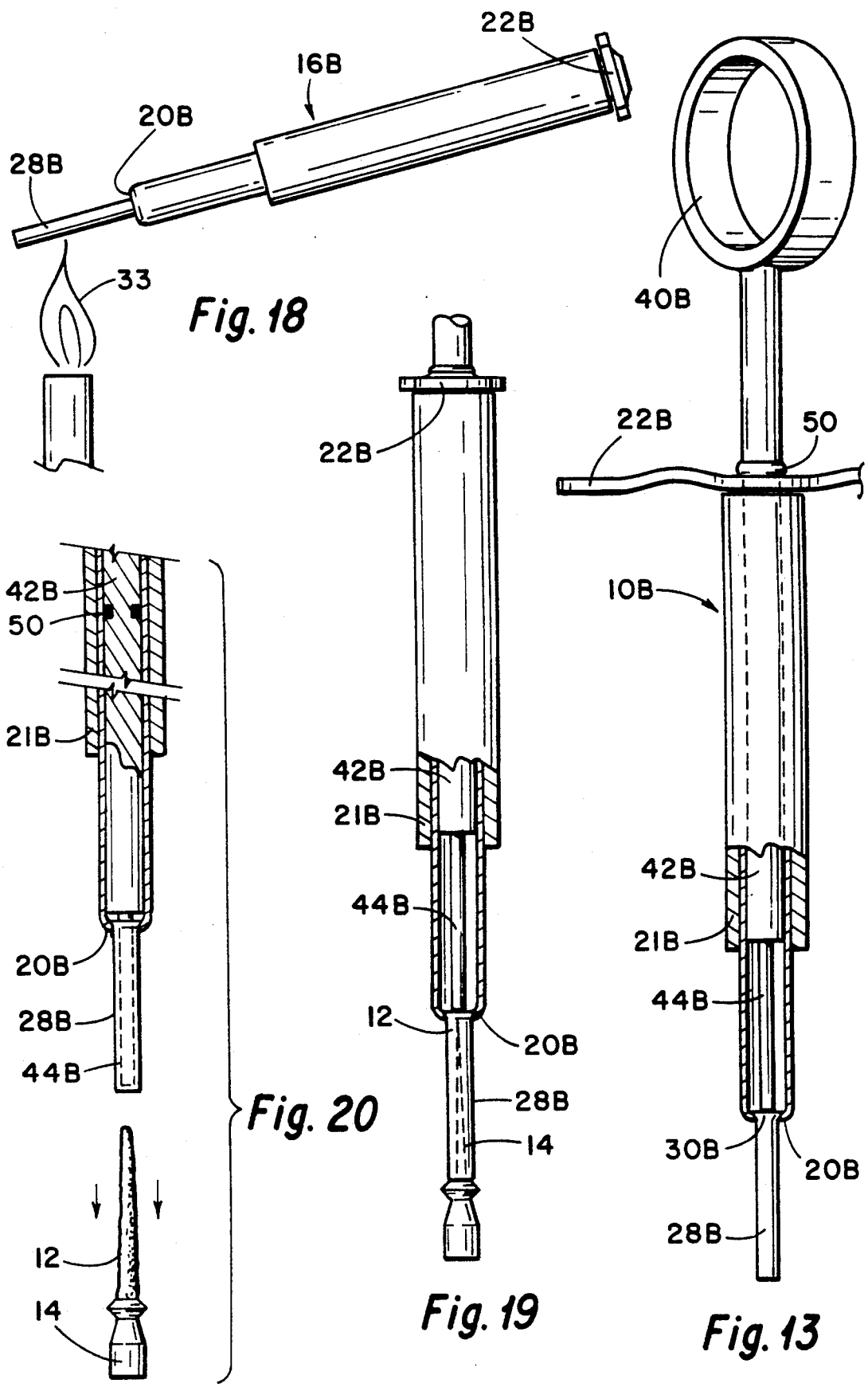

METHOD AND APPARATUS FOR APPLYING GUTTA PERCHA TO A CARRIER

BACKGROUND OF THE INVENTION

1. Field of the Invention

The present invention relates generally to the field of endodontics and more specifically to a method for preparing a gutta percha coated carrier used in obturating an extirpated root canal.

2. Description Of The Related Art

Current methods of obturating (filling) an extirpated (stripped) root canal commonly involve packing a root canal with a thermoplastic material, such as gutta percha, so that the root canal space is filled with the thermoplastic material. Preferably, the space is filled with the thermoplastic material forming a seal which prevents leakage between the root canal and the surrounding tissue.

It has been found that a satisfactory seal can be formed by softening the gutta percha by heating it prior to inserting it into the root canal. Normally, the gutta percha is applied to a carrier prior to insertion into the root canal in order to facilitate insertion. Carriers pre-coated with gutta percha are known, as shown by U.S. Pat. No. 4,758,156 issued on Jul. 19, 1988 to the inventor of the present invention and which is incorporated herein by reference. However, carriers pre-coated with gutta percha are expensive to purchase, and a less expensive means is desired for applying gutta percha to a carrier.

U.S. Pat. No. 5,067,900 issued Nov. 26, 1991 to inventor, McSpadden, teaches an inexpensive method of applying gutta percha to a carrier. The McSpadden patent teaches use of a syringe whose barrel is pre-filled with sufficient gutta percha to coat a plurality of carriers. According to the teachings of McSpadden, the amount of gutta percha applied to a carrier is dependent on the forca exerted on the plunger of the syringe and upon the rate of withdrawal of the coated carrier from the discharge end of the syringe. One problem with this method is that the person coating the carrier must be steady-handed in order to obtain a uniform and consistent coating of the carrier. Steady handiness is difficult with the McSpadden device since the entire syringe body is hot due to the preheating necessary to increase the plasticity of the gutta percha.

Also another problem with multiple usage syringes, such as the McSpadden syringe, is that if the carrier is inserted into the root canal to test the sizing fit prior to applying the gutta percha to the carrier, as is the common practice, it may be coated with debris that could contaminate the community pool of gutta percha of the syringe.

The present invention provides a reliable, easy to use, and inexpensive method for applying a uniform coating of gutta percha to a carrier without contamination problems, as it employs a single dosage, disposable source of gutta percha.

SUMMARY OF THE INVENTION

Briefly, the present invention is a method and a syringe-type device for applying gutta percha to a carrier which will later be employed to obturate an extirpated root canal. The steps of the method consist of: (1) inserting a cennula filled with a measured amount of gutta percha into a barrel cavity provided in a barrel of the syringe-type device so that an upper lip provided on the cannula seats in a mating reduced diameter section of the barrel cavity, (2) applying heat to the cannula to increase the plasticity of the gutta percha, (3) inserting a carrier into a lower open end of the cannula, and (4) pushing a plunger provided in the device downward by means of a ring attached to an upper end of the plunger and by means of finger tabs provided on a plunger insertion end of the barrel so that a reduced cylindrical portion of the plunger provided on a lower end of the plunger enters an upper open end of the cannula and pushes the carrier, to which the gutta percha is now applied, out of the lower open end of the cannula and out of the device at its dispensing end. The barrel is provided with an insulating sleeve to prevent fingers from contacting the heated barrel as the fingers push the plunger downward.

Alternately, the device may be modified by replacing the plunger with an alternate plunger designed to accommodate an alternate cannula which is provided with its own attached dispensing cannula plunger. In this alternate embodiment, the alternate plunger is pushed downward against the dispensing cannula plunger and the dispensing cannula plunger is pushed from the alternate cannula's upper open end to its lower open end, thus pushing the gutta percha coated carrier out of the lower open end of the alternate cannula and out of the dispensing end of the device.

BRIEF DESCRIPTION OF THE DRAWINGS

FIG. 1 is a from elevation of the device for applying gutta percha to a carrier according to a preferred embodiment of the present invention, showing a carrier inserted into the dispensing end of the device.

FIG. 2 is a front elevation of the device of FIG. 1 showing the gutta percha coated carrier after it is pushed out of the dispensing end of the device.

FIG. 3 is an enlarged partial front elevation of the device for applying gutta percha to a carrier according to another embodiment of the present invention, showing a gutta percha containing alternate cannula provided with its own cannula plunger.

FIG. 4 is a slightly enlarged front elevation of a plunger removed from the device of FIG. 1.

FIG. 5 is a top plan elevation of the plunger of FIG. 4.

FIG. 6 is a slightly enlarged front elevation of a barrel removed from the device of FIG. 1.

FIG. 7 is a top plan elevation of the barrel of FIG. 6.

FIG. 8 is a left side elevation of the barrel of FIG. 6.

FIG. 9 is a front elevation of a gutta percha containing cannula for use with the device of FIG. 1.

FIG. 10 is a cross-sectional view of the cannula taken along line 10—10 of FIG. 9.

FIG. 11 is a left side elevation of the barrel illustrating insertion of the cannula into the barrel via a side opening provided in the barrel.

FIG. 12 is a left side elevation of the barrel illustrating the cannula being heated after it is inserted into the barrel.

FIG. 13 is a front elevation of a second alternate embodiment of the device for applying gutta percha to a carrier according to the present invention, shown loaded with a cannula of gutta percha.

FIG. 14 is a front elevation of a second alternate barrel removed from the device of FIG. 13 showing the cannula being loaded therein.

FIG. 15 is a top plan view of the second alternate barrel taken along line 15—15 of FIG. 14.

FIG. 16 is a front elevation of a second alternate plunger removed from the device of FIG. 13.

FIG. 17 is a top plan view of the second alternate plunger of FIG. 16.

FIG. 18 is a left side elevation of the second alternate barrel illustrating the cannula being heated after it is loaded into the second alternate barrel.

FIG. 19 is a partial front elevation of the device of FIG. 13, showing a carrier inserted into the dispensing end of the device.

FIG. 20 is the device of FIG. 19, showing the gutta percha coated carrier after it is pushed out of the dispensing end of the device.

DETAILED DESCRIPTION OF THE PREFERRED EMBODIMENTS

Referring now to the drawings and initially to FIGS. 1 and 2, there is illustrated a syringe-type device 10 for applying gutta percha 12 or other suitable thermoplastic material (not illustrated) to a carrier 14 according to a preferred embodiment of the present invention.

The device 10 is provided with a barrel 16, illustrated in FIGS. 6, 7, and 8, having a plunger insertion end 18 and an opposite dispensing end 20. Adjacent the plunger insertion end 18, the barrel 16 is provided externally with an insulating sleeve 21 which prevents fingers (not illustrated) from contacting the barrel 16 after the barrel 16 is heated, as will be described more fully hereinafter. The plunger insertion end 18 is also provided with a pair of outward extending finger tabs 22, one finger tab 22 being provided on either side of the barrel 16. A barrel cavity 24 communicates between the plunger insertion end 18 and the dispensing end 20. Adjacent the dispensing end 20, the barrel 16 is provided with an opening 26 which communicates with the barrel cavity 24.

As illustrated in FIGS. 9, 10 and 11, a cannula 28 pre-filled with gutta percha 12 inserts into the barrel cavity 24 by way of opening 26. The cannula 28 is provided with an upper open end 29 and an opposite lower open end 31 and is hollow between the upper and lower open ends 29 and 31. The gutta percha 12 is pre-filled in the hollow cannula 28 between the upper and lower ends 29 and 31. Once inserted into the barrel cavity 24, the cannula 28 is pushed toward the dispensing end 20 until an upper lip 30 provided on the cannula 28 seats into a mating reduced diameter section 32, best seen in FIGS. 6 and 8, provided in the barrel cavity 24. The reduced diameter section 32 is located so that when the cannula 28 is seated therein, the open lower end 31 of the cannula 28 is approximately flush with the dispensing end 20.

As shown in FIG. 12, once the cennula 28 is seated in the reduced diameter section 32, the gutta percha 12 is then heated by means of a flame 33 or other suitable heat source (not illustrated) in order to increase the plasticity of the gutta percha 12 in preparation for inserting it into a root canal (not illustrated). The device 10 is preferably constructed of metal or other suitable material to enable the device to withstand heating of the gutta percha 12 when the cannula 28 is contained therein.

As illustrated in FIGS. 1, 4, and 5, the device 10 is provided with a plunger 34 having an upper end 36 and an opposite lower end 38. The upper end 36 is provided with a ring 40 which attaches to one end of a cylindrical main body 42 provided on the plunger 34. The main body 42 attaches by an opposite end to a reduced cylindrical portion 44 which forms the lower end 38.

The cylindrical main body 42 has an outside diameter slightly smaller than an inside diameter of the barrel cavity 24, and the reduced cylindrical portion 44 has an outside diameter slightly smaller than an inside diameter of the cannula 28. The lower end 38 of the plunger 34 inserts into the barrel cavity 24 at the plunger insertion end 18 of the barrel 16, and the plunger 34 moves downward in the barrel cavity 24 until the lower end 38 touches the heated gutta percha 12 contained within the cannula 28. Movement of the plunger 34 is facilitated by inserting a thumb (not illustrated) into the ring 40 and placing middle and index fingers (not illustrated) of the same hand (not illustrated) as the thumb (not illustrated) under the finger tabs 22 and pressing the fingers (not illustrated) toward the thumb (not illustrated).

As illustrated in FIGS. 1 and 2, a carrier 14 is then inserted into the heated cannula 28 via the dispensing end 20. The plunger 34 is then pushed downward, thus pushing the carrier 14, which is now coated with gutta percha 12, out of the device 10. The carrier 14 is then ready for use in a root canal (not illustrated).

An alternate device 10A is illustrated in FIG. 3. This embodiment is used in conjunction with an alternate cannula 28A which is provided with its own dispensing cannula plunger 46. In this embodiment, the barrel 16 is employed and an alternate plunger 34A is used which is identical to the plunger 34 except that the reduced cylindrical portion 44 is eliminated. Similar to the first embodiment, the alternate cannula 28A is inserted into the barrel 16 and is heated. Thereafter, the alternate plunger 34A is inserted into the barrel cavity 24 and pushed downward until the alternate plunger 34A engages the dispensing cannula plunger 46. At this point, a carrier 14 is inserted into the heard cannula 28A via the dispensing end 20. The alternate plunger 34A is then pushed downward, thus pushing the dispensing cannula plunger 46 downward through the alternate cannula 28A and pushing the carrier 14, which is now coated with gutta percha 12, out of the alternate device 10A. The carrier 14 is then ready for use in a root canal (not illustrated).

A second alternate device 10B is illustrated in FIGS. 13 through 20. This embodiment is provided with an alternate barrel 16B, illustrated in FIGS. 14 and 15. The alternate barrel 16B has an alternate plunger insertion end 18B and an opposite alternate dispensing end 20B. Adjacent the alternate plunger insertion end 18B, the alternate barrel 16B is provided externally with an alternate insulating sleeve 21B similar to the insulating sleeve 21 described for the first embodiment of the device 10. The alternate plunger insertion end 18B is likewise provided with a pair of outwardly extending alternate finger tabs 22B, one alternate finger tab 22B being provided on either side of the alternate barrel 16B. An alternate barrel cavity 24B communicates between the alternate plunger insertion end 18B and the alternate dispensing end 20B. The alternate barrel cavity 24B is provided with an alternate mating reduced diameter section 32B at the alternate dispensing end 20B, with the remaining length of the alternate barrel cavity 24B being uniform in internal diameter.

As illustrated in FIG. 14, a second alternate cannula 28B, pre-filled with gutta percha 12 between its second alternate cannula open upper end 29B and its opposite second alternate cannula lower end 31B, is inserted into the alternate barrel insertion end 18B of the alternate barrel cavity 24B. The second alternate cannula 28B is then pushed toward the alternate dispensing end 20B until the second alternate cannula open lower end 31B extends outward from the alternate dispensing end 20B and the second alternate cannula 28B is secured by an alternate upper lip 30B provided on the second alternate cannula open upper end 29B which seats into the alternate mating reduced diameter section 32B of the alternate barrel cavity 24B.

As shown in FIG. 18, once the second alternate cannula 28B is seated in the alternate mating reduced diameter section 32B, the gutta percha 12 is heated by means of the flame 33 or other suitable heat source (not illustrated) in order to increase the plasticity of the gutta percha 12 in preparation for inserting a carrier 14 into the second alternate cannula 28B. The second alternate device 10B, although not directly heated by the flame 33 in this embodiment, is preferably constructed of metal or other suitable material to enable the second alternate device 10B to withstand heat transferred to it by means of the attached alternate cannula 28B as it is heated.

As illustrated in FIGS. 16 and 17, the second alternate device 10B is provided with a second alternate plunger 34B having an alternate upper end 36B and an opposite alternate lower end 38B. The alternate upper end 36B is provided with an alternate ring 40B which attaches to one end of an alternate cylindrical main body 42B provided on the second alternate plunger 34B. The alternate cylindrical main body 42B attaches by an opposite end to an alternate reduced cylindrical portion 44B which forms the alternate lower end 38B.

The alternate cylindrical main body 42B has an outside diameter smaller than an inside diameter of the alternate barrel cavity 24B, and the alternate reduced cylindrical portion 44B has an outside diameter slightly smaller than an inside diameter of the second alternate cannula 28B. The alternate cylindrical main body 42B is provided with circumferential groove 48 therearound into which an O-ring 50 inserts. As the alternate cylindrical main body 42B is pushed through the alternate barrel cavity 24B and the alternate reduced cylindrical portion 44B is simultaneously pushed through the second alternate cannula 28B, the O-ring 50 movably engages the alternate barrel cavity 24B.

The purpose of the O-ring 50 is to provide frictional resistance to movement of the second alternate plunger 34B within the alternate barrel 16B and thereby enabling the user to more precisely control movement of the second alternate plunger 34B.

After the second alternate cannula 28B is heated, the second alternate plunger 34B is inserted into the alternate barrel 16B at the alternate plunger insertion end 18B and is moved downward into the alternate barrel cavity 24B until the alternate lower end 38B touches the heated gutta percha 12 contained with the second alternate cannula 28B. Movement of the second alternate plunger 34B is facilitated by inserting a thumb (not illustrated) into the alternate ring 40B and placing middle and index fingers (not illustrated) of the same hand (not illustrated) as the thumb (not illustrated) under the alternate finger tabs 22B and pressing the fingers (not illustrated) toward the thumb (not illustrated).

As shown in FIG. 19, the carrier 14 is then inserted into the heated second alternate cannula 28B via the second alternate cannula open lower end 31B. As shown in FIG. 20, the second alternate plunger 34B is then pushed downward, thus pushing the carrier 14, which is now coated with gutta percha 12, out of the second alternate device 10B. The coated carrier 14 is then ready for use in a root canal (not illustrated).

Although not illustrated, the second alternate device 10B may be employed with the alternate cannula 28A, shown in FIG. 3. This may be done by either using the alternate reduced cylindrical portion 44B to engage the dispensing cannula plunger 46 or, alternately, by modifying the second alternate plunger 34B so as to eliminate the alternate reduced cylindrical portion 44B. If the alternate reduced cylindrical portion 44B is eliminated, the alternate cylindrical main body 42B serves as the alternate lower end 38B of the second alternate plunger 34B which is engagable with the dispensing cannula plunger 46.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A method of applying gutta percha to a carrier comprising the following steps:
    (a) inserting a cannula which is pre-filled with gutta percha into a barrel cavity provided in a barrel of a syringe-type device so that a lower open end of the cannula is adjacent a dispensing end of the syringe-type device;
    (b) heating the gutta percha in order to thermally increase the plasticity of the normally viscous gutta percha, which step can be accomplished either before or after (a);
    (c) inserting the carrier into the lower open end of the cannula; and
    (d) pushing the carrier and gutta percha out the lower open end by means of a plunger movably provided in the barrel cavity.

2. A method of applying gutta percha to a carrier according to claim 1 wherein the cannula of step (a) is provided with its own dispensing cannula plunger.

3. A method of applying gutta percha to a carrier according to claim 1 wherein the cannula is inserted into the barrel cavity by means of an opening provided in the barrel.

4. A device for applying gutta percha to a carrier comprising:
    a barrel provided with a barrel cavity communicating between a plunger insertion end and an opposite dispensing end;
    means for gripping the barrel being provided on the barrel;
    means for retaining a cannula which is pre-filled with gutta percha in the barrel cavity so that an elongated shaft portion of an endodontic filler carrier is insertable into the cannula when the gutta percha is heated in order to thermally increase the plasticity of the normally viscous gutta percha;
    a plunger movable within the body cavity, an upper end of the plunger being provided with means for gripping the plunger, an opposite lower end of the plunger being provided with means for dispensing the carrier and gutta percha from the device; and an insulating sleeve on the exterior of said barrel and adjacent said plunger insertion end.

5. A device for applying gutta percha to a carrier according to claim 4 wherein the means for gripping the barrel are finger tabs provided on the plunger insertion end so that the finger tabs are provided on either side of the barrel and extend outward therefrom.

6. A device for applying gutta percha to a carrier according to claim 4 further comprising the barrel being provided with an opening which communicates with the barrel cavity and through which the cannula inserts into the barrel cavity.

7. A device for applying gutta percha to a carrier according to claim 4 wherein the means for retaining the cannula within the barrel cavity comprises a reduced diameter section provided in the barrel cavity which mates with an upper lip provided on the cannula.

8. A device for applying gutta percha to a carrier according to claim 4 wherein the means for gripping the plunger is a ring.

9. A device for applying gutta percha to a carder according to claim 4 wherein the means for dispensing the carrier and gutta percha from the device comprises a reduced diameter section being provided on the lower end of the plunger, said reduced diameter section being movable through the cannula.

10. A device for applying gutta percha to a carrier according to claim 4 wherein the means for dispensing the carrier and gutta percha from the device comprises a cylindrical main body of the plunger which engages a dispensing cannula plunger provided on the cannula so that the dispensing cannula plunger moves through the cannula.

11. A device for applying gutta percha to a carrier according to claim 4 wherein the device is constructed of material capable of withstanding heating of the gutta percha contained within the cannula.

12. A device for applying gutta percha to a carrier according to claim 4 wherein said cannula is dimensioned to contain a single application of gutta percha in order to prevent cross contamination of carriers.

13. A method of applying gutta percha to a carrier comprised of the following steps:
 (a) inserting a cannula which is pre-filled with gutta percha through a barrel cavity provided in a barrel of a syringe-type device until an upper open end of the cannula is secured to a dispensing end of the syringe-type device and an opposite lower open end of the cannula extends outward from the dispensing end;
 (b) heating the gutta percha in order to thermally increase the plasticity of the normally viscous gutta percha, which step can be accomplished either before or after (a);
 (c) inserting a plunger into a barrel cavity until it touches the gutta percha;
 (d) Inserting the carrier into the lower open end of the cannula; and
 (e) pushing the carrier and gutta percha out of the lower open end by means of the plunger.

14. A method of applying gutta percha to a carrier according to claim 13 wherein the cannula of step (a) is provided with its own dispensing cannula plunger.

15. A device for applying gutta percha to a carrier comprising:
 a barrel provided with a barrel cavity communicating between a plunger insertion end and an opposite dispensing end;
 means for gripping the barrel being provided on the barrel;
 means for retaining a cannula which is pre-filled with gutta percha in said dispensing end of said barrel cavity so that a carrier is insertable into a lower open end provided on the cannula;
 a plunger movable within said body cavity, an upper end of the plunger being provided with means for gripping the plunger, an opposite lower end of the plunger being provided with means for dispensing the carrier and gutta percha from the device; and
 an insulating sleeve provided externally on said barrel and adjacent said plunger insertion end.

16. A device for applying gutta percha to a carrier according to claim 15 wherein the means for gripping the barrel are finger tabs provided on the plunger insertion end so that the finger tabs are provided on either side of the barrel and extend outward therefrom.

17. A device for applying gutta percha to a carrier according to claim 15 wherein the means for retaining the cannula at the dispensing end of the barrel cavity comprises a reduced diameter section provided at the dispensing end of the barrel cavity which mates with an upper lip provided on an upper open end of the cannula.

18. A device for applying gutta percha to a carrier according to claim 15 wherein the means for gripping the plunger is a ring.

19. A device for applying gutta percha to a carrier according to claim 15 wherein the means for dispensing the carrier and gutta percha from the device comprises a reduced diameter section being provided on the lower end of the plunger, said reduced diameter section being movable through the cannula.

20. A device for applying gutta percha to a carrier according to claim 15 wherein the means for dispensing the carrier and gutta percha from the device comprises a cylindrical main body of the plunger which engages a dispensing cannula plunger provided on the cannula so that the dispensing cannula plunger moves through the cannula.

21. For use in dispensing small quantities of thermoplastic filler material, such as gutta percha, for use in filling an extirpated root canal of a tooth by use of a carrier having an elongated shaft portion of dimension to be received in the extirpated root canal, apparatus comprising:
 a tubular metal cannula having an intermediate body portion and an inlet end and an outlet end and of internal diameter sufficient to fully receive therein a carrier shaft portion, the outlet end being of the same internal and external diameter as said intermediate portion and said inlet end having an integral enlarged external diameter flared portion; and
 thermoplastic filler material substantially filling said tubular cannula, the filler material having viscosity such that it remains within said tubular cannula at ambient temperatures, the tubular cannula being formed of a heat conductive metal whereby the filler material can be heated by applying heat to the exterior of the cannula to increase the viscosity of the filler material whereby the filler material will adhere to the shaft portion of a carrier when inserted into said tubular cannula outlet end.

22. A method of applying gutta percha to a carrier for use in filling an extirpated root canal of a tooth, the carrier having an elongated shaft portion, comprising the following steps:
  (a) inserting a cannula that is pre-filled with gutta percha into a barrel cavity provided in a barrel of a syringe-type device so that an open outlet end of the cannula is adjacent a dispensing end of the syringe-type device, the cannula being of elongated tubular open ended construction of length as great as said carrier shaft portion;
  (b) heating the gutta percha by applying heat externally of the cannula in order to thermally increase the plasticity of the normally viscous gutta percha, which step can be accomplished either before or after step (a);
  (c) inserting substantially the full length of the carrier shaft portion into the lower open end of the cannula; and (d) pushing the carrier and gutta percha out the cannula lower open end by means of a plunger movably provided in the barrel cavity to coat the carrier shaft portion with heated gutta percha.

23. A method of applying gutta percha to a carrier for use in filling an extirpated root canal of a tooth the carrier having an elongated shaft portion, comprised of the following steps:
  (a) inserting a cannula which is pre-filled with gutta percha through a barrel cavity provided in a barrel of a syringe-type device until an upper open end of the cannula is secured to a dispensing end of the syringe-type device and an opposite lower open end of the cannula extends outward from the dispensing end, the cannula being of elongated tubular open ended construction of length as great as said carrier shaft portion;
  (b) heating the gutta percha by applying heat externally of the cannula in order to thermally increase the plasticity of the normally viscous gutta percha, which step can be accomplished either before or after (a);
  (c) inserting substantially the full length of the elongated shaft portion of the carrier into the lower open end of the cannula;
  (d) inserting a plunger into the barrel cavity until it touches the gutta percha; and
  (e) pushing the carrier and gutta percha out of the lower open end by means of the plunger to coat the carrier shaft portion with heated gutta percha.

* * * * *